United States Patent [19]

Esanu

[11] 4,256,767

[45] Mar. 17, 1981

[54] PHENOXY ALKYLAMIDES

[75] Inventor: André Esanu, Paris, France

[73] Assignee: Societe d'Etudes de Produits Chimiques, Paris, France

[21] Appl. No.: 50,106

[22] Filed: Jun. 19, 1979

[30] Foreign Application Priority Data

Jun. 22, 1978 [AU] Australia ............................. PD4821

[51] Int. Cl.³ .................. A61K 31/18; A61K 31/165; C07C 143/72; C07C 103/19
[52] U.S. Cl. .................................. 424/324; 424/321; 564/154; 564/83; 564/86
[58] Field of Search ......... 260/559 T, 556 S, 556 AR; 424/324, 321

[56] References Cited

U.S. PATENT DOCUMENTS 3,426,067 2/1969 Weber et al. ..................... 424/321 X Primary Examiner—Frederick E. Waddell
Attorney, Agent, or Firm—Eyre, Mann, Lucas & Just

[57] ABSTRACT

A new phenoxy alkylamide is disclosed. The compound has been found to have beneficial activity in the field of immuno-stimulation.

2 Claims, No Drawings

PHENOXY ALKYLAMIDES

The present invention relates to new phenoxy alkylamide especially interesting in the field of immuno-stimulation. These compounds are: N-{(2-mercaptoethyl carbamoyl) ω-alkyl}phenoxy alkylamides which may be represented by the general formula:

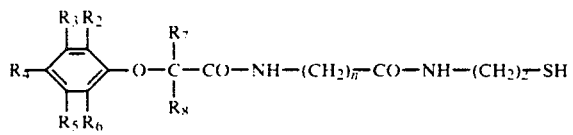

wherein at least one of the R is not hydrogen, with:
- $R_3$ and $R_5$ each stand for H, lower alkyl up to $C_5$ or t-butyl,
- $R_2$ and $R_6$ each stand for H, lower alkyl up to $C_5$ or $-SO_2NH_2$,
- $R_4$ stands for H, lower alkyl or alkoxy up to $C_5$, aryl or aryloxy group, halogen, a hydroxy group or $-SO_2NH_2$,
- $R_7$ and $R_8$ each stand for H or lower alkyl up to $C_5$, and n is an integer from 2 to 5 included.

These compounds may be readily prepared by the reaction of phenoxy alkyl carbamoyl alkyl cyanide of the formula:

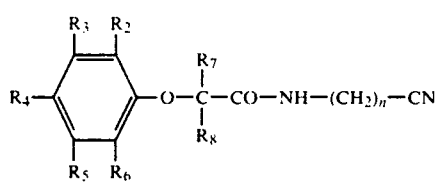

on an excess of cysteamine in a polar solvent at the boil and then treating the compound thus obtained at a temperature of 40° to 80° C. by a hydrochloric solution.

The invention will be better understood from the following examples:

EXAMPLE 1: N-{(2-mercaptoethyl carbamoyl)2-ethyl}p-chlorophenoxy isobutyramide In a half-liter reactor fitted with stirring and warming means are poured 130 ml of methanol, 12.8 g (0.048 mol) of 2-(p-chlorophenoxy isobutyramide)ethyl cyanide, then under stirring 18.5 g (0.24 mol) of cysteamine.

The reacting mixture is then refluxed for 5 hours, which leads to an oily product and a precipitate which is treated by diethyl ether, washed with the same product until neutral pH and then placed in a one liter reactor with 350 ml of water and submitted to a continuous nitrogen flow; a hydrochloric solution 0.1 N is added slowly until pH 4.5 (14 ml) and the mixture is warmed at 55°-60° C. for 5 hours.

It is then cooled and the precipitate appears which is separated, washed with water, then with diethyl ether; after retreatment of the diethyl ether phasis and obtention of a new precipitate, both precipitates are gathered, washed with water, dried, which leads to 14 g (84%) of a white crystalline product melting at 118° C. (Tottoli), the analysis of which shows a perfect correspondence with the formula $C_{15}H_{21}N_2O_3SCl$. This compound is insoluble in water and soluble in ethanol, dimethylsulphoxide, transcutanol and chloroform.

EXAMPLE 2: N-{(2-mercaptoethyl carbamoyl)2-ethyl}3',5'-di-t-butyl phenoxy isobutyramide The method of Example 1 was repeated but 2-(p-chlorophenoxy isobutyramide) ethyl cyanide was replaced by (3,5-di-t-butyl phenoxy isobutyramide) ethyl cyanide. There was obtained, with a yield of 67%, a white crystalline product melting at 113°-114° C. (Tottoli), the analysis of which shows a perfect correspondence with the formula $C_{23}H_{38}N_2O_3S$. This compound is insoluble in water. The starting (3,5-di-t-butyl phenoxy isobutyramide) ethyl cyanide was prepared from 3,5-di-t-butyl phenol and α-bromo isobutyramide ethyl cyanide in the presence of Na, in ethanol.

EXAMPLE 3: N-{(2-mercaptoethyl carbamoyl)2-ethyl}p-chlorophenoxy acetamide

The method of Example 1 was repeated but 2-(p-chlorophenoxy acetamide) ethyl cyanide was used instead of 2-(p-chlorophenoxy isobutyramide) ethyl cyanide. There was obtained with a yield of 63%, a white crystalline product melting at 113° C. (Tottoli), the analysis of which shows a perfect correspondence with the formula $C_{13}H_{17}ClN_2O_3S$. This compound is insoluble in water at room temperature but soluble in DMSO and transcutanol.

Toxicity

LD 50 has been determined per os on female mice. The compounds of the invention present a toxicity higher than 5 g/kg.

Pharmacology

The compounds of the invention have a very favorable action, with a protection rate of 100% on mice (swiss or C 3 mice infested by $10^4$ Salmonella thyphimurium-stock C 5, very pathogenic), with a single dose of 1 mg/mouse, administered per os, 10 days before the infection.

All the treated mice were still alive 17 days after the infection. 50% of the non-treated animals were dead on the 6th day and 100% on the 9th day (experiment performed on batches of 20 mice).

The muramyl dipeptide, considered as reference product (see L. CHEDID et al.: Proc. Nat. Acad. Sci. U.S.A., 74, 2089–2093, 1977 and L. CHEDID et E. LEDERER, Biochemical Pharmacology, 27, 2183–2186, 1978) used in the same conditions, has resulted in no significant survival compared with control animals.

The compounds present the same efficiency at the dose of 0.5 mg/mouse but only if they are administered between −14 and −10 days before the infection. At the dose of 1 mg/mouse, they are efficient, when administered between the days −14 and −6.

The increase in the protection rate goes together with an increase in the rate of antibodies producted by the lymphocitary cells of the tested animals compared with the control animals.

Thus, these compounds act as an immuno-stimulant.

Posology

In human therapeutics, normal doses are 0.1 g to 1 g, 3 to 5 times at each season.

I claim:
1. New phenoxy alkylamide derivatives of the formula:

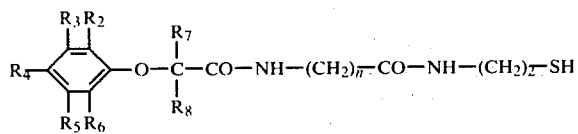

wherein at least one of the R is not hydrogen, with:

$R_3$ and $R_5$ each stand for H, lower alkyl up to $C_5$ or t-butyl, $R_2$ and $R_6$ each stand for H lower alkyl up to $C_5$ $R_4$ stands for H or halogen, $R_7$ and $R_8$ each stand for H, or lower alkyl up to $C_5$, and n is an integer from 2 to 5 included.

2. A therapeutic composition of matter acting as an immuno-stimulating agent containing as active ingredient, an effective amount of a compound as defined in claim 1.

* * * * *

UNITED STATES PATENT AND TRADEMARK OFFICE
CERTIFICATE OF CORRECTION

PATENT NO. : 4,256,767
DATED : March 17, 1981
INVENTOR(S) : Andre Esanu

It is certified that error appears in the above-identified patent and that said Letters Patent are hereby corrected as shown below:

Column 2, line 59: change "tested" to --treated--.

Column 4, line 3: insert --or-- after "H".

Signed and Sealed this

Second Day of June 1981

[SEAL]

Attest:

RENE D. TEGTMEYER

Attesting Officer

Acting Commissioner of Patents and Trademarks